United States Patent
Noonan et al.

(10) Patent No.: US 11,793,578 B2
(45) Date of Patent: Oct. 24, 2023

(54) OPTICAL SHAPE SENSING FOR INSTRUMENT TRACKING IN ORTHOPEDICS

(71) Applicant: KONINKLIJKE PHILIPS N.V., Eindhoven (NL)

(72) Inventors: David Paul Noonan, New York, NY (US); Molly Lara Flexman, Melrose, MA (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1714 days.

(21) Appl. No.: 15/509,502

(22) PCT Filed: Aug. 25, 2015

(86) PCT No.: PCT/IB2015/056416
§ 371 (c)(1),
(2) Date: Mar. 8, 2017

(87) PCT Pub. No.: WO2016/038489
PCT Pub. Date: Mar. 17, 2016

(65) Prior Publication Data
US 2017/0281282 A1 Oct. 5, 2017

Related U.S. Application Data

(60) Provisional application No. 62/047,326, filed on Sep. 8, 2014.

(51) Int. Cl.
*A61B 34/20* (2016.01)
*A61B 17/15* (2006.01)
(Continued)

(52) U.S. Cl.
CPC ............ *A61B 34/20* (2016.02); *A61B 17/154* (2013.01); *A61B 17/1764* (2013.01);
(Continued)

(58) Field of Classification Search
CPC .............. A61B 17/154; A61B 17/1764; A61B 2034/2055; A61B 2034/2061; A61B 34/20; G02B 6/4292
See application file for complete search history.

(56) References Cited

U.S. PATENT DOCUMENTS

2009/0137952 A1* 5/2009 Ramamurthy ........... A61B 5/06
604/95.01
2011/0098533 A1* 4/2011 Onoda ................. A61B 1/0051
600/117
(Continued)

*Primary Examiner* — Yi-Shan Yang
*Assistant Examiner* — Alexei Bykhovski (57) ABSTRACT

An optical shape sensing system includes an attachment mechanism (130) being configured to secure an optical shape sensing fiber to an instrument, the optical shape sensing fiber being connected to the instrument and configured to identify a position and orientation of the instrument. An optical shape sensing module (115) is configured to receive feedback from the optical shape sensing fiber and register the position of the instrument relative to an operating environment. A position response module (144) is configured to provide feedback to an operator based on position or orientation of the instrument to guide usage of the instrument.

15 Claims, 6 Drawing Sheets

(51) Int. Cl.
*A61B 17/17* (2006.01)
*G02B 6/42* (2006.01)

(52) U.S. Cl.
CPC .... *G02B 6/4292* (2013.01); *A61B 2034/2055* (2016.02); *A61B 2034/2061* (2016.02)

(56) References Cited

U.S. PATENT DOCUMENTS

| | | | |
|---|---|---|---|
| 2011/0319714 A1* | 12/2011 | Roelle | A61B 1/00006 600/118 |
| 2013/0060278 A1 | 3/2013 | Bozung | |
| 2013/0188855 A1 | 7/2013 | Desjardins et al. | |
| 2013/0281990 A1* | 10/2013 | Manzke | A61B 17/00234 606/1 |
| 2014/0275997 A1* | 9/2014 | Chopra | A61B 5/064 600/424 |
| 2016/0015293 A1* | 1/2016 | Denissen | A61B 5/0422 600/424 |

* cited by examiner

OPTICAL SHAPE SENSING FOR INSTRUMENT TRACKING IN ORTHOPEDICS

CROSS-REFERENCE TO PRIOR APPLICATIONS

This application is the U.S. National Phase application under 35 U.S.C. § 371 of International Application Serial No. PCT/IB2015/056416, filed on Aug. 25, 2015, which claims the benefit of U.S. application Ser. No. 62/047,326, filed on Sep. 8, 2014. These applications are hereby incorporated by reference herein.

BACKGROUND

Technical Field

This disclosure relates to medical instruments and more particularly to shape sensing optical fibers in medical applications for tracking medical instruments during computer aided procedures.

Description of the Related Art

Computer assisted surgery (CAS) systems are used for preoperative planning and intra-operative surgical navigation. In this context, preoperative planning refers to any computer assisted determination of surgical steps, such as cutting, incisions, targeting, etc. Planning can occur before or during a procedure. The preoperative planning often uses 2D or 3D images of a patient using any medical imaging modality (computed tomography (CT), magnetic resonance imaging (MRI), ultrasound, X-ray, endoscopy, etc.) or anatomical models (e.g., a knee model). In the context of CAS, surgical navigation refers to live tracking of instruments and patient anatomy enabling surgeons to precisely execute the preoperative plan. Surgical navigation is implemented using tracking technologies.

An example of tracking technology is line-of-sight optical tracking. Line-of-sight optical tracking technology uses an optical camera either operating in the visible or infra-red range. The camera is configured to detect markers in its field of view and infer position and orientation of arrangement of markers based on their relative position. Commonly, two or more cameras arranged in a known configuration are used to enable stereo vision and depth perception. This tracking technology requires un-interrupted line-of-sight between the camera(s) and the markers.

Total knee replacement requires that portions of the femur and tibia bones be removed and replaced with implantable artificial components. CAS is used in total knee replacement to plan the appropriate cut planes using the preoperative planning module and to enable execution of the plan by tracking bone and instruments during the procedure. The bones are often resected with the use of cutting blocks that guide the cutting planes so that they are correctly positioned and angled to accept and align the artificial components to be implanted. CAS aims to improve both the position and orientation of the cutting block and of the subsequent implants to return the joint to its optimal biomechanics.

A line-of-sight optical tracked CAS system for total knee replacement involves a set of line-of-sight optical tracking attachments that are attached to the patient to provide anatomical tracking. A line-of-sight optical tracking attachment is rigidly attached to the bone through one or more screws and extends a distance away from the bone. In total knee replacement these trackers are attached to both the femur and tibia to provide the live anatomical tracking.

Existing optical CAS systems suffer from a number of disadvantages. Line-of-sight optical CAS systems require an unobstructed path between the detection cameras and the tracking attachments. Any tracking attachments that are not visible by the cameras cannot provide a valid measurement. It can be difficult to maintain an unobstructed path during all parts of the procedure, especially when, e.g., a bone is manipulated to test the dynamic biomechanics. These CAS systems not only require line-of-sight, but are also only accurate within a defined volume. This volume is with respect to the camera position and can be difficult to maintain throughout the procedure, especially during manipulation of the joint. To achieve the required accuracy, line-of-sight CAS systems typically use reflective balls arranged into optical tracking attachments which can have lengths up to 20 cm in the largest dimension. Such large attachments limit the physical workspace available to the clinicians and risk collisions intra-operatively. Due to the size and weight of the optical tracking attachments, a large screw pin is needed to rigidly and accurately attach to the bone. In some cases two screw pins are needed for a single tracking attachment. These screw pins can lead to adverse effects such as stress fractures (especially in the case of two pins used close together), infection, nerve injury, pin loosening (leading to additional pins or inaccuracies in the measurement), etc.

Electromagnetic (EM) navigation systems also suffer from a number of disadvantages. Similar to line-of-sight tracking, it can be difficult to maintain an optimal clinical workflow while also satisfying the requirements of the EM system. The EM system only provides accurate measurements within a defined volume with respect to position of the field generator. Further, metal in the EM field can generate interference and degrade the accuracy of the measurement.

SUMMARY

In accordance with the present principles, an optical shape sensing system includes an attachment mechanism being configured to secure an optical shape sensing fiber to an instrument, the optical shape sensing fiber being connected to the instrument and configured to identify a position and orientation of the instrument. An optical shape sensing module is configured to receive feedback from the optical shape sensing fiber and register the position of the instrument relative to an operating environment. A position response module is configured to provide feedback to an operator based on position or orientation of the instrument to guide usage of the instrument.

Another optical shape sensing system includes an optical shape sensing module configured to receive feedback from one or more optical shape sensing fibers. One or more instruments have at least one optical shape sensing fiber connected thereto, the optical shape sensing fiber being employed to positionally track the instrument in an operating environment. A position response module is configured to provide feedback to an operator based on position or orientation of the instrument to guide usage of the instrument based on a surgical plan. An anatomical map is included of a region in the operating environment wherein positions of the one or more instruments are tracked relative to the anatomical map.

A method for tracking instruments using optical shape sensing includes securing an optical shape sensing fiber to an instrument, the optical shape sensing fiber being connected to the instrument and configured to identify a position of the instrument; registering a position of the instrument relative to a stored image of an operating environment; receiving feedback from the optical shape sensing fiber to determine a current position; and guiding use of the instrument based upon the position and orientation of the instrument.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, systems and methods are provided for optical shape sensing that can be used for displaying relative positions of instruments, fixtures, mechanical components, etc. on an anatomic map or other image during a surgical procedure. In one embodiment, the optical shape sensing fiber can be attached or mounted in or on a tool, instrument, fixtures, etc. The optical shape sensing measurement can be registered to the anatomical map. The position of the optical shape sensing markers with respect to an anatomic map can be displayed for a user. The optical shape sensing fiber may be attached to orthopedic or other instruments such as drills and cutting rigs to track their positions. In additional, optical shape sensing may be employed for tracking soft tissue and/or bones in orthopedic procedures. Optical shape sensing systems may be attached to the bones, ligaments, skin, inserts, etc. or combinations thereof.

In accordance with the present principles, optical shape sensing is employed for tracking instruments in orthopedic or other procedures. The optical shape sensing fiber(s) may be permanently embedded within instruments or be temporarily attached to instruments. Registration methods between the instrument with the optical shape sensing fiber(s) (OSS sensor) and patient coordinate systems are also described. The use of optical shape sensing enabled tools is also described, focusing on intelligent tools that can inform an operator when they are in the correct position or provide limits for safety or other purposes.

Optical shape sensing (OSS) uses light along a multicore optical fiber to reconstruct the shape along that fiber. The principle involved makes use of distributed strain measurement in the optical fiber using characteristic Rayleigh backscatter or controlled grating patterns.

The shape along the optical fiber begins at a specific point along the sensor, known as the launch or $z=0$, and the subsequent shape position and orientation are relative to that point. The optical fiber may be, e.g., 200 microns in diameter and can be up to a few meters long while maintaining millimeter-level accuracy. Optical shape sensing fibers can be integrated into a wide range of medical devices to provide live guidance medical procedures. As an example, a guidewire or catheter may be employed for navigation to an artery with the optical shape sensing measurement overlaid upon a pre-operative image.

In accordance with the present principles, OSS fiber sensors are employed which have a small footprint and a light-weight nature to provide the ability to track and integrate shape sensed instruments. Tracking instruments intra-operatively provides the opportunity to improve the accuracy of implant placement and ultimately clinical outcome. In addition, safety can be improved by ensuring position awareness of instruments (and in particular cutting instruments) with respect to the patient's anatomy during manipulation.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
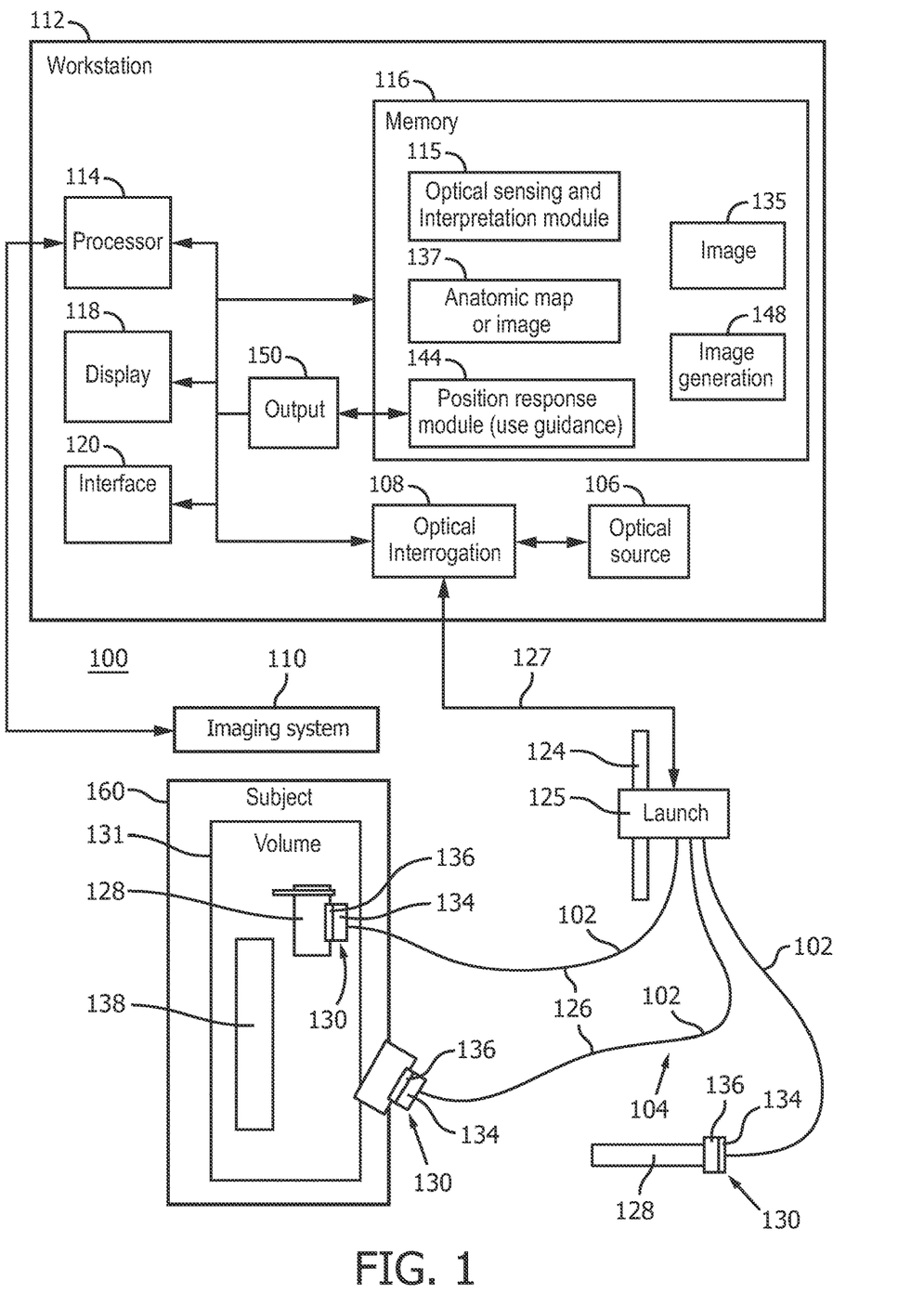
FIG. 1 is a block/flow diagram showing a shape sensing system for tracking instruments in an operating environment in accordance with one embodiment.

Referring now to the drawings in which like numerals represent the same or similar elements and initially to FIG. 1, a system 100 for optical shape sensing guidance in orthopedic and other applications using shape sensing enabled devices is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an optical sensing module 115 configured to interpret optical feedback signals from a shape sensing device or system 104. Optical sensing and interpretation module 115 is configured to use the optical signal feedback (and any other feedback, e.g., electromagnetic (EM) tracking) to reconstruct deformations, deflections and other changes associated with bones or joint positions or positions of other anatomical features, including skin, ligaments, tendons, muscles and other materials or tissues.

The shape sensing system 104 includes one or more optical fiber sensors 102. Each sensor 102 includes optical fibers 126 which are configured in a set pattern or patterns. The optical fibers 126 connect to the workstation 112 through a launch mount 125 and cabling 127. The cabling 127 may include fiber optics, electrical connections, other instrumentation, etc., as needed. The cabling 127 interfaces with an optical interrogation unit 108 that may include or work with an optical source or sources 106. The interrogation unit 108 sends and receives optical signals from the shape sensing system 104. An operating room rail 124 may include the launch mount 125 that include a reference point or launch point (z=0) for the one or more optical sensors 102.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

Inherent backscatter in conventional optical fiber can be exploited for optical shape sensing (OSS). One such approach uses Rayleigh scatter (or other scattering) in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

Fiber Bragg Gratings (FBGs) may also be employed for OSS, which use Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of OSS is that various sensor elements can be distributed over the length of a fiber. Incorporating three or more cores with various sensors (gauges) along the length of a fiber that is embedded in a structure, permits a three dimensional form of such a structure to be precisely determined with high accuracy. Along the length of the fiber, at various positions, a multitude of FBG sensors can be located. From the strain measurement of each FBG, the curvature of the structure can be inferred at that position. From the multitude of measured positions, the total three-dimensional form is determined.

In one embodiment, the one or more optical sensors 102 are connected to one or more instruments 128. Instruments 128 may include a number of different categories of devices, tools, fixtures, attachments, etc. For example, numerous different instruments 128 may be employed during orthopedic surgery. These instruments 128 can be broadly separated into two categories, e.g., those which are handheld by a surgeon or operator and those which are physically attached to a patient or subject 160. For illustrative purposes, examples of such instruments 128 that may be attached to the patient may include cutting blocks, jigs, screws, pins, trial implants, etc., and examples of such instruments 128 that may be handheld by the surgeon or operator may include a registration pointer, a bone drill, a bone saw, bone osteomes (similar to chisels), a scalpel, forceps, aspiration devices, etc. In some embodiments, the instruments 128 may include a probe, an endoscope, a robot, an electrode, a drill, a cutting rig or other medical component, etc.

In particularly useful embodiments, OSS fiber sensors 102 may be attached to the instrument(s) 128 in a number of ways. For example, attachment of the fiber sensor 102 may be permanent. For instruments such as a bone drill or bone saw, it may be desirable to have a dedicated OSS fiber sensor 102 permanently attached to, or embedded within, the instrument 128. The fiber sensor 102 could enter the instrument 128 through an electrical cable (where available) or other accessory, for example. The fiber sensor 102 could be terminated within a handle of the instrument 128, or within an instrument tool tip. Alternatively, attachment of the fiber sensor 102 may be temporary. For example, for instruments such as osteomes or cutting blocks, having a permanent attachment of the fiber sensor 102 to the instrument 128 may not be desirable or cost effective. An alternative to the permanent attachment is a feature(s) on the instrument 128 where an OSS fiber sensor 102 could be temporarily affixed. Such an embodiment would have an attachment mechanism 130 having two or more mating attachment points 134, 136—one on the distal end of the OSS tether, and the other on the instrument itself.

On the instrument side, the attachment point 136 could be an integral part of the instrument design, or could be retrofit and affixed with screws, clamps, glue or similar mechanisms. Temporary fixation methods such as magnets, clasps, snap-fits, etc. could be employed to allow the attachment point 134 on the fiber sensor 102 to attach and detach to the attachment point 134 on the instrument 128. The attachment mechanism 130 preferably includes an interface between the attachment points 134 and 136 to only attach in a specific way (i.e., only one way) to ensure a correct orientation of the instrument 128 is known.

Workstation 112 includes an image generation module 148 configured to receive feedback from the shape sensing system 104 and record position (and orientation) data as to where the one or more optical sensors 102 have been within a volume 131. An image 135 of the one or more optical sensors 102 or a virtual representation of the instrument 128 to which the fiber is attached, within the space or volume 131 can be displayed on a display device 118. Workstation 112 includes the display 118 for viewing internal images of a subject (patient) or volume 131 and may include the image 135 as an overlay or other rendering of the sensing device 104 on images collected by an imaging device 110. The imaging device 110 may include any imaging system (e.g., computed tomography (CT), ultrasound, fluoroscopy, magnetic resonance imaging (MRI), etc.). Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

The system 100 is based on optical shape sensing and can be used for displaying the positions of instruments 128 overlaid on an anatomic map 137 (e.g., an anatomical image of volume 131) during a surgical procedure or otherwise. The system 100 includes the integration of the optical shape sensing fibers 102 into instruments 128 which may be compared to anatomical positions of a patient 160 (e.g., the skin, muscle, ligaments, bones, etc.). By registering of the optical shape sensing sensors 102 to the anatomical map 137 to display of the position(s) of the optical shape sensing sensors 102 and therefore the instruments 128 connected thereto, limits and warnings may be provided to the user to alert of potential damage or operation outside the intended boundaries set forth in a plan or other criteria.

The optical sensors 102 may have their coordinate systems registered to one or more reference positions, a global coordinate system or any other coordinate system. Optical shape sensing fibers 102 can be registered to each other using multiple techniques including shape-to-shape registration, mechanical registration of launch positions, point-based registration, etc. To make the shape sensing measurements useful to the clinician, the measurements can be provided in the context of an anatomic map 137. The anatomical map can be a pre-operative image (such as, a CT, MRI, fluoroscopy or ultrasound image) or intra-operative image (e.g., live). In some cases, an anatomical model is morphed to match the feature measurements during a registration step. Herein, a 3D surface or volume acquired preoperatively or from any source will be referred to as a model.

Once the optical shape sensing fiber 102 is placed and registered to the anatomical map or other reference (e.g., bone 138), the fiber positions can be displayed to the operator (e.g., on display 118). The display of OSS data on an anatomical map may take many forms and provide a plurality of functions.

The system 100 permits more accurate placement of instruments 128, e.g., the cutting and drilling guides, as well as instruments to create needed cuts and holes. However, knowledge of the position and orientation of the instruments 128 also permits for additional 'intelligent' functionality to be added. In one example, automatic control of cutting surfaces is provided by a position response module 144. When using shape sensing cutting instruments, such as a bone drill or a bone saw, it is possible to actively stop the drill bit or saw blades based on the known position of the cutting surfaces with respect to the patient anatomy. The instrument's speed or other function may be changed in accordance with its position. In one embodiment, the surgeon could denote virtual 'safe zones' within which the cutting instruments would automatically switch off or operation of the instrument is changed.

The position response module 144 is configured to provide feedback to an operator based on position or orientation of the instrument to guide usage of the instrument 128. The position response module 144 may be configured to control instrument function based on a position of the instrument relative to an identified zone in the operating environment; to provide feedback to an operator when the instrument is positioned with a particular orientation or location; halt use of the instrument when the instrument's position changes or initiates function of the instrument when the instrument's position changes. The feedback provided to the user may include e.g., audio, visual, haptic, etc., provided through an output device 150 that may be located on the console 112 on the instrument 128 or provided through other methods, e.g., through interface 120, display 118, etc.

In another example, operator feedback (e.g., audio, visual, haptic, etc.) can be provided by the module 144 (through the instrument 128) when an instrument is positioned with a correct orientation. Correctly positioning and orienting the instruments 128 is an important parameter for ensuring correct implant placement or for other tasks. For this reason, cutting and drilling guides are conventionally employed. As an additional input for the surgeon, when the position and orientation of a handheld instrument 128 lies within a threshold of a desired position, the system could alert the operator using auditory, visual, haptic or tactile feedback (e.g., through interface 120 or instrument 128). In yet another example, instrument-to-bone contact may be sensed using the control module 144. For embodiments where the OSS fiber sensor 102 is permanently embedded within the instrument 128, the integration could be designed such that instrument contact with the bone is detected. Such an embodiment would be particularly suited for registration instruments which are employed as part of the initial point-based registration (i.e., a registration pointer). Such an embodiment could also be employed for force sensing of the contact force between the instrument and the bone.

In still another example, automatic positioning of the cutting or drilling guides may be performed using the control module 144. A mechatronically (e.g., mechanical and electronic) actuated cutting guide (128) which is registered to the patient, and can automatically set the optimum cutting planes based on a pre-procedure plan, may be employed. This replaces purely manual adjustments of the cutting and drilling guides into their needed positions. These conventional manual adjustment steps take place after the cutting guide is initially attached to the bone, and the range of motion is very limited.

The present principles apply to any use of an optical shape sensing fiber for surgical guidance and navigation. In particularly useful embodiments the present principles may be employed in knee replacement surgery, anterior cruciate ligament (ACL) repair, hip replacement, brain surgery, elbow surgery and other such applications. In addition, the OSS may employ any type of reflective or scattering phenomena such as, e.g., Rayleigh scatter (enhanced and regular) as well as Fiber Bragg implementations of shape sensing fiber. The present principles may be employed with manual and robotic navigation systems.

Figure 2A:
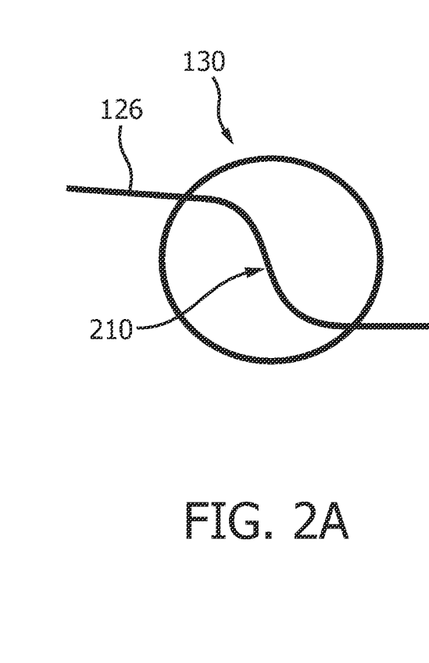
FIG. 2A is a diagram showing a button fixation mechanism with an s-shaped fiber path in accordance with one embodiment.
Figure 2B:
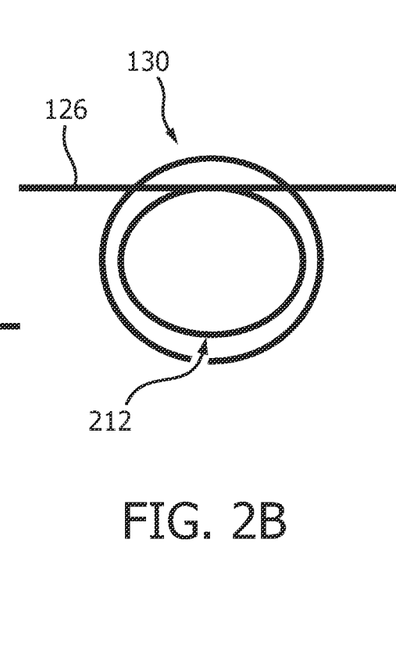
FIG. 2B is a diagram showing a button fixation mechanism with a loop-shaped fiber path in accordance with one embodiment.
Figure 2C:
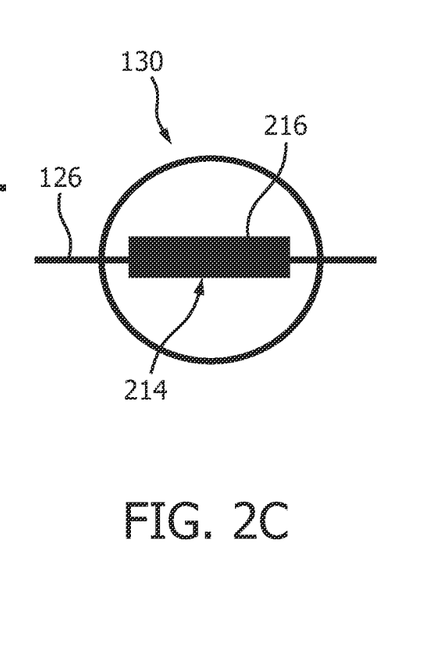
FIG. 2C is a diagram showing a button fixation mechanism with a straight fiber path embedded in material in accordance with one embodiment.

Referring to FIGS. 2A-2C, example configurations for attaching optical fibers for optical shape sensing to an attachment mechanism 130 (e.g., formed from points 134 and 136) are illustratively shown. The optical shape sensing fiber 126 can be attached to the attachment mechanism 130 in multiple ways. Mechanical clamping of optical fiber 126 into the attachment mechanism 130 (with or without the optical fiber coating intact) may include a groove or path in which the fiber rests as depicted in FIGS. 2A and 2B. The path may include predetermined shapes such as an s-shape 210 (FIG. 2A or a loop 212 (FIG. 2B). In the example of FIG. 2C, a straight portion 214 of the fiber is embedded in a material 216 of the attachment mechanism 130 while the curved portions are freely deformable about the attachment mechanism 130 in space. Any other shape of embedded fiber (other than the loop 212 or s-shape 210, for example) can also be employed.

The fiber 126 may be connected using an adhesive or clamp on the optical fiber 126 into the attachment mechanism 130 (with or without the optical fiber coating intact). Alternately, a free floating fiber 126 may be passed through a known shape that can be optically tracked (shape-sensed). A combination of these and/or other attachment modes are also contemplated.

In one embodiment, the optical fiber 126 is permanently attached to the attachment mechanism 130. In another embodiment, the attachment mechanism 130 can split apart such that one half of attachment mechanism 130 is permanently attached to a fixation portion and the other half is attached to the OSS tether (fiber 126).

Figure 3:
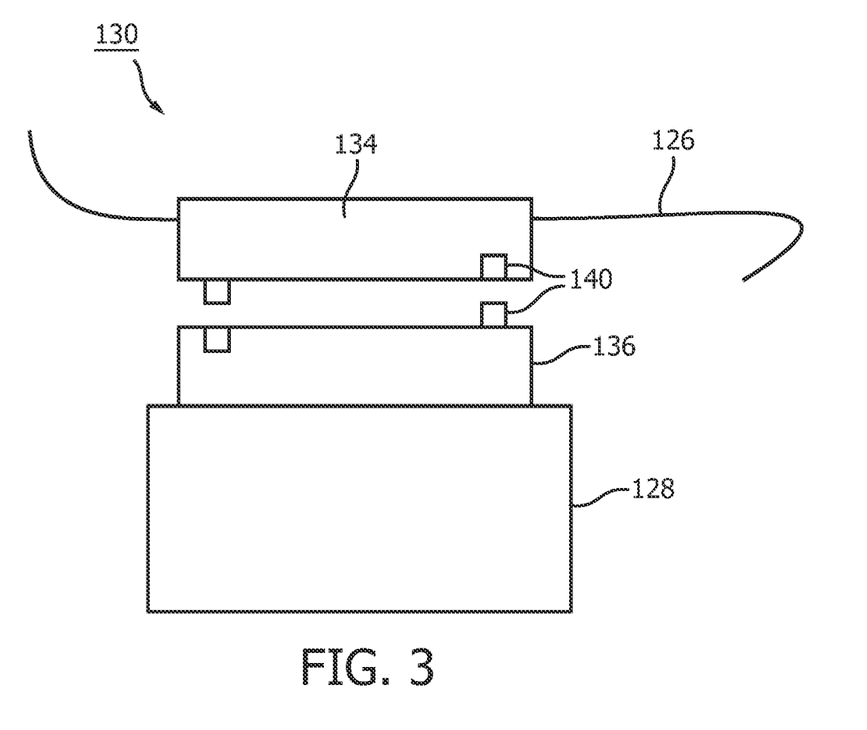
FIG. 3 is a diagram showing a spilt-half button fixation mechanism used as an attachment device in accordance with one embodiment.

Referring to FIG. 3, the split-half attachment mechanism 130 can split apart to permit mating attachment points 134, 136 to be connected and disconnected by the clinician as needed. The clinician can then attach or join the two halves 134, 136 together at an appropriate point during the procedure. The mating attachment points 134, 136 would preferably only join together in one specific orientation (e.g., they would be keyed) using mating mechanical parts 140. Connecting the mating attachment points 134, 136 could be achieved using a fastener (not shown), such as, e.g., clips, clasps, screws, magnets, etc. This split half button configuration permits one OSS tether (fiber 126) to be used in multiple ways during the procedure, e.g., by attaching it to different mating attachment points 134 on the instruments 128.

Figure 4:
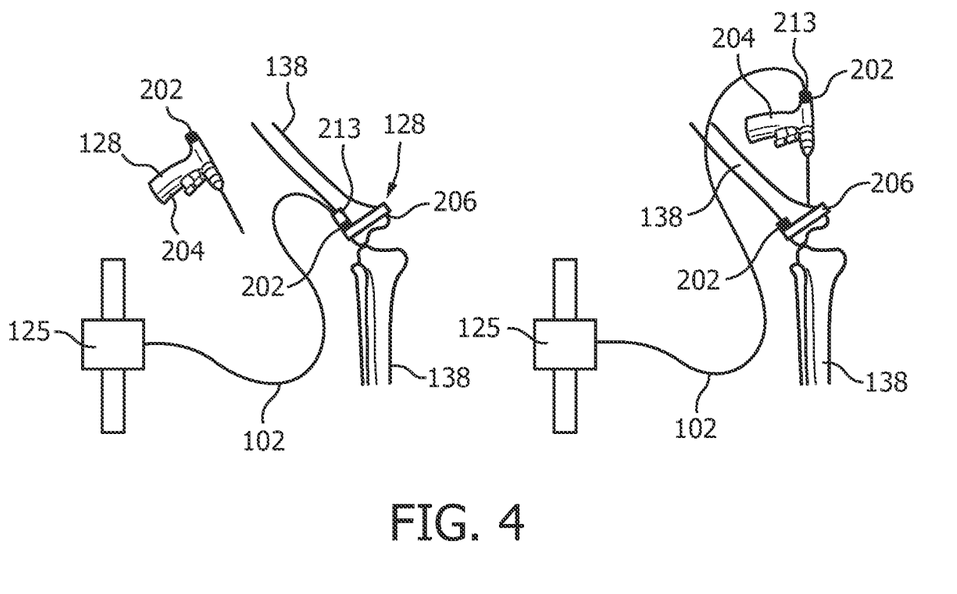
FIG. 4 is a diagram showing interchangeability of optical fiber sensors between instruments in accordance with useful embodiments.

Referring to FIG. 4, in accordance with the present principles, optical fiber sensors 102 may be configured to be detachable and capable of being connected to a plurality of different instruments 128. Each instrument 128 features an attachment point 202 configured to receive a mating portion 213 of an optical fiber sensor 102. FIG. 4 illustratively shows a bone drill 204 and a cutting block 206 employed in orthopedic surgical procedures. The optical fiber sensor 102 features the mating portion 213 at its distal tip. The optical fiber sensor 102 can be manually transferred between instruments (204, 206).

One advantage of such a temporary attachment scheme includes that a single fiber sensor 102 could be switched between multiple different instruments over the course of a procedure thus minimizing the number of OSS consoles needed. In an additional embodiment, a single optical fiber sensor 102 with multiple attachment points 202 along its length may also be employed. In such an implementation, several instruments may be tracked concurrently with one fiber sensor 102.

Figure 5:
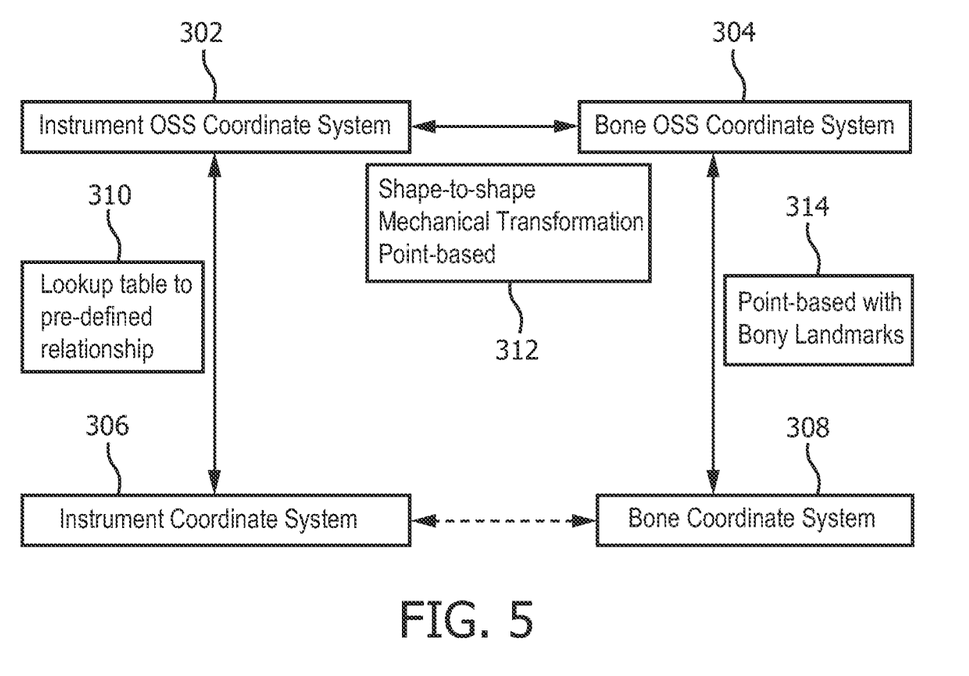
FIG. 5 is a diagram showing registration between instrument, optical sensing fibers and bone coordinate systems in accordance with one embodiment.

Referring to FIG. 5, four coordinate systems are illustratively depicted that may be registered together, and three registrations are shown that can occur to track an instrument 128 within a bone coordinate system. The three registrations include registration 310: from Instrument coordinate system 306 to Instrument OSS sensor coordinate system 302; registration 312: Instrument OSS sensor coordinate system 302 to Bone OSS sensor coordinate system 304 and registration 314: Bone OSS sensor coordinate system 304 to Bone coordinate system 308.

The instrument coordinate system 306 is registered to the OSS sensor 302 tracking the instrument. This may be done a-priori and found using, e.g., a lookup table. The OSS sensor tracking the instrument and the bone can be registered in many ways (e.g., shape-to-shape registration, point-based registration, or in the simplest case, a known mechanical transformation between their origins). The Bone coordinate system 308 is registered to the OSS sensor 302 tracking the bone using body landmarks, e.g., of the knee. Once the three registrations 310, 312, 314 take place, the instrument is registered to the bone.

Figure 6:
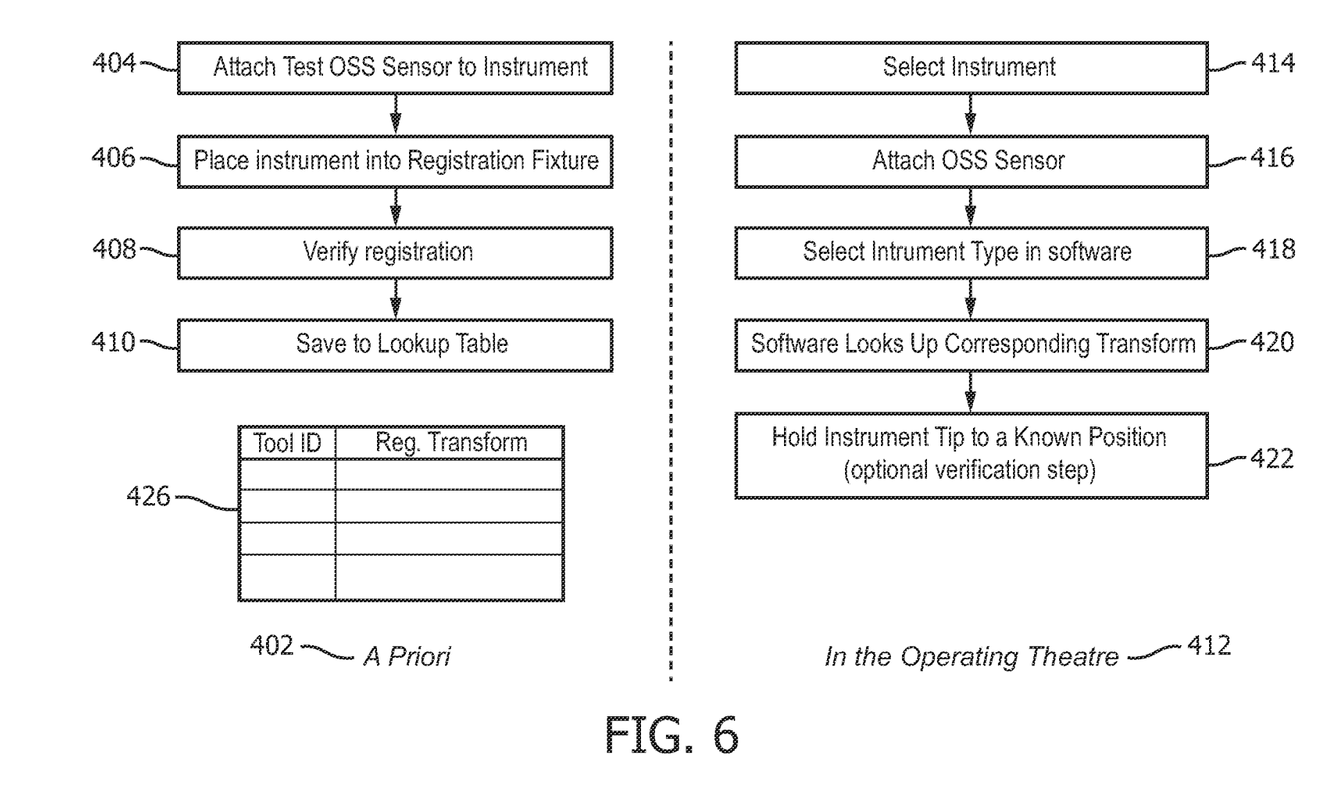
FIG. 6 is a diagram showing registration workflow in accordance with one embodiment.

Referring to FIG. 6 with continued reference to FIG. 5, an illustrative workflow for registration between an instrument 128 and an optical fiber sensor 102 is shown. The workflow may be divided into operational regimes, e.g., a-priori 402 and operating theater 412. In block 404, a test optical fiber sensor may be attached to the instruments. In block 406, the instrument with the sensor attached is placed into a registration fixture. The registration fixture may include known positions to test or initialize the registration of the instruments with the sensor. In block 408, registration is verified and a transform may be provided between the instrument coordinate system (306) and the sensor coordinate system (302). This provides the registration 310. In block 410, the verified registration transform is saved to, e.g., a lookup table 426. An initial transformation can be generated depending on the type of instrument or attachment device. The look-up table 426 indexes instrument identification (instrument ID) data to a corresponding transform to be employed as will be described. The look-up table 426 or similar memory structure can be used to hold the registration between the instrument (128) and the sensor (102). An accurate transformation of each instrument with respect to the fiber attachment point would be generated separately and be accessible within the OSS user interface. It is also possible that a registration fixture could be placed onsite in the operating theatre 412 for live registration between the sensor (102) and the instrument (128).

Instrument coordinate system (306) to Instrument OSS sensor coordinate system (302) registration 310 may include permanent attachment/integration of the sensor (102) into the instrument (128). In this case, at the time of integration or attachment to the instrument, the sensor needs to be registered to that instrument. This can be done by placing the instrument (128) with the sensor (102) into the registration fixture. This fixture can be, e.g., a mold of the instrument or can be a dynamic fixture that moves the instrument in a known way (such as a pivot fixture) thereby giving the appropriate transformation. In another embodiment, a re-attachable sensor (102) is placed onto the instrument (128). In this case, the fiber attachment takes on a known mechanical position and orientation with respect to the instrument (for example, a clamp onto a feature of the instrument). In a laboratory setting a representative sensor, instrument, and attachment can be used to generate the transformation. This could also be known mechanically by the design of the attachment. In any case, a transformation is determined and stored.

In the operating theater 412, an instrument (128) is selected for tracking in block 414. When a given instrument is activated or selected, a member of the operating theatre staff could select the appropriate instrument from a library. Alternatively, automatic detection of the correct instrument could be implemented using radiofrequency identification (RFID) or a similar device identification method. An optical fiber sensor (102) is attached to the instrument (128) in block 416. The instrument type (instrument ID) is selected in software in block 418. The software looks up a corresponding transform from the look-up table 426 in block 420. Using this information, the registrations 312 and 314 may be performed.

Instrument OSS sensor coordinate system 302 to bone OSS sensor coordinate system 304 registration 312 may be made if registration to bones is preferred. OSS tracked instruments would likely be employed in conjunction with OSS tracking of the bones themselves and that all elements would be registered into the one coordinate system. This can be easily achieved by ensuring Launch Fixtures of the fiber(s) tracking the bones and the fiber(s) tracking the instruments are fixed with a known geometric relationship. If they are not in a known geometric relationship, registration between shape coordinate systems can be accomplished with point-based or shape-to-shape registration. In the case of a single sensor approach, the instrument and the bones are automatically within the same coordinate system. Bone OSS sensor coordinate system 304 to Bone coordinate system 308 registration 314 can be performed by point-based registration of bony landmarks. Other registration techniques may also be employed. In block 422, an optional verification step may be performed. This may include holding the instrument tip to a known position and comparing the results.

It should be understood that the embodiments described herein illustratively employ a knee joint. However, any joint or other anatomical feature, prosthetic or model may employ the present principles. In addition, the embodiments described herein may be combined to further increase the advantages of the present principles. For example, the sutured OSS fiber embodiments may be combined with the skin attached OSS fiber and/or the sleeve with integrated OSS fiber.

Figure 7:
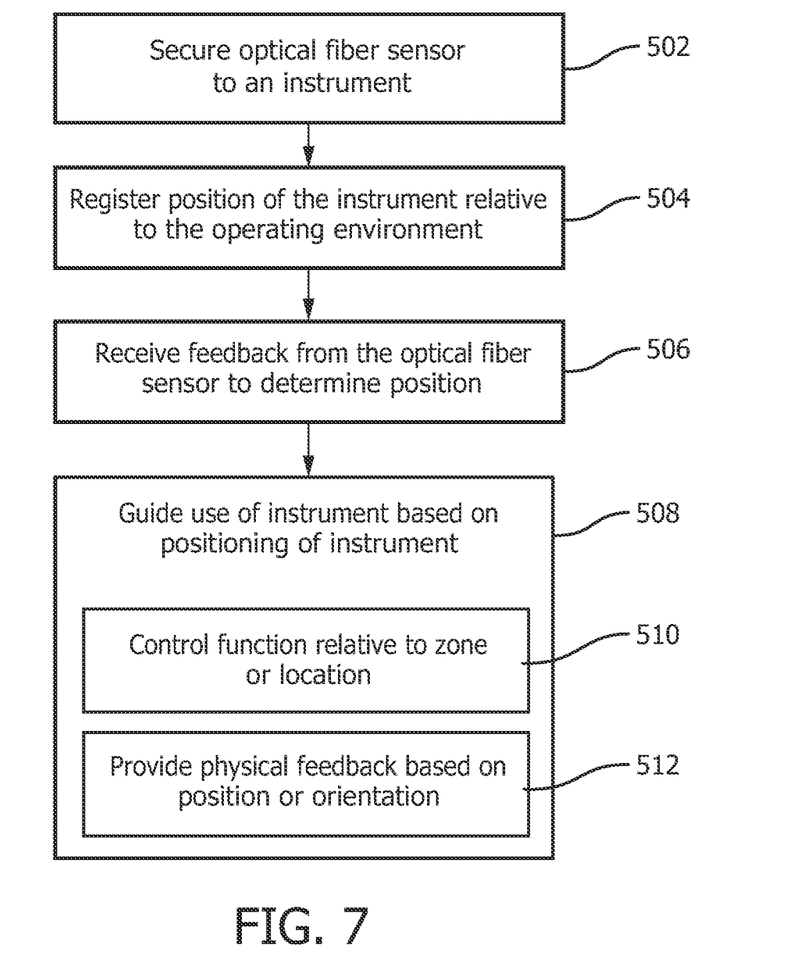
FIG. 7 is a flow diagram showing a method for shape sensed tracking of instruments in accordance with illustrative embodiments.

Referring to FIG. 7, methods for tracking instruments using optical shape sensing are illustratively shown. In block 502, an optical shape sensing fiber is secured to an instrument. The optical shape sensing fiber is connected to the instrument and configured to identify a position of the instrument. The optical shape sensing fiber may be interchangeably mounted on a plurality of instruments.

In block 504, a position of the instrument is registered relative to a stored image of an operating environment. The operating environment may include an operating room for a medical procedure and a position of the instrument may be tracked relative to an anatomical map. In block 506, feedback is received from the optical shape sensing fiber to determine position (and orientation) of the instrument. The positional information is employed to provide informational feedback to the user. This information may take many forms. For example, the user may receive a signal that the instrument being tracked is correctly positioned. The user may receive feedback that the instrument has moved out of range or has exceeded a safety zone. The user may receive feedback on whether the instrument is permitted for placement in a particular region.

In block 508, instrument function may be guided in its use or function based on the position of the instrument or force/strain applied to the instrument. Guided use here means to provide information that extends or improves the use of the instrument or makes the instrument safer to use. For example, in block 510, the instrument is controlled based on a position of the instrument relative to an identified zone in the operating environment. This may include turning off an instrument if the identified zone, e.g., a safety zone is exited. In one example, when the proper depth is reached a drill is switched off or a warning is displayed or sounds. In another embodiment, an instrument may be inserted until a surface is detected, e.g., instrument contact with bone. Use of the instrument may be initiated or halted when the instrument's position changes or when a measured force or strain measurement exceeds a threshold. The function of the instrument may be made proportional to the position change or measured force or strain.

In block 512, position feedback (e.g., physical feedback) may be provided to an operator when the instrument is positioned with a particular orientation. For example, when the instrument is properly aligned, an indicator may be provided, e.g., a light, sound, vibration, message, etc. This also includes adjusting cutting guides or the like by permitting automatic positioning of the guided along axes provided in a given coordinate system and/or in accordance with a plan.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for optical shape sensing for instrument tracking in orthopedics (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. An optical shape sensing system, comprising:
an attachment mechanism being configured to secure an optical shape sensing fiber to an instrument, the optical shape sensing fiber being connected to the instrument and configured to identify a position and orientation of the instrument;
an optical shape sensing module configured to receive feedback from the optical shape sensing fiber and register the position of the instrument relative to an operating environment; and
a position response module configured to provide feedback to an operator based on position or orientation of the instrument to guide usage of the instrument.

2. The system as recited in claim 1, wherein the attachment mechanism includes a detachable device configured to connect with a portion of the instrument.

3. The system as recited in claim 2, wherein the detachable device includes mateable portions to connect and disconnect from the instrument.

4. The system as recited in claim 3, wherein the detachable device is interchangeably mountable on a plurality of instruments.

5. The system as recited in claim 1, wherein the optical shape sensing module is further configured to track a position of the instrument relative to an anatomical map.

6. The system as recited in claim 1, wherein the position response module is further configured to control instrument function based on a position of the instrument relative to an identified zone or position in the operating environment.

7. The system as recited in claim 1, wherein the position response module is further configured to provide feedback to an operator when the instrument is positioned with a particular orientation.

8. The system as recited in claim 1, wherein the position response module is further configured to initiate or halt use of the instrument when the instrument's position changes.

9. An optical shape sensing system, comprising:
an optical shape sensing module configured to receive feedback from one or more optical shape sensing fibers;
one or more instruments having at least one optical shape sensing fiber connected thereto to positionally track the instrument in an operating environment;
a position response module configured to provide feedback to an operator based on position or orientation of the instrument to guide usage of the instrument based on a surgical plan; and
an anatomical map included in a region of the operating environment wherein positions of the one or more instruments are tracked relative to the anatomical map.

10. The system as recited in claim 9, wherein the at least one optical shape sensing fiber is detachably mounted to the one or more instruments by a detachable device including mateable portions to connect and disconnect from an instrument.

11. The system as recited in claim 10, wherein the mateable portions are interchangeably mountable on a plurality of instruments.

12. The system as recited in claim 9, wherein the position response module is further configured to control instrument function based on a position of the instrument relative to an identified zone or position in the operating environment.

13. The system as recited in claim 9, wherein the position response module is further configured to provide feedback to an operator when the instrument is positioned with a particular orientation.

14. The system as recited in claim 9, wherein the position response module is further configured to initiate or halt use of the instrument when the instrument's position changes.

15. A method for tracking instruments using optical shape sensing, comprising:
securing an optical shape sensing fiber to an instrument, the optical shape sensing fiber being connected to the instrument and configured to identify a position of the instrument;
registering a position of the instrument relative to a stored image of an operating environment;
receiving feedback from the optical shape sensing fiber to determine a current position; and
guiding use of the instrument based upon the position and orientation of the instrument.

* * * * *